(12) United States Patent
Deng (10) Patent No.: US 6,500,169 B1
(45) Date of Patent: Dec. 31, 2002

(54) POWERED SURGICAL HANDPIECE WITH MEMBRANE SWITCH

(75) Inventor: Wenjie Deng, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 09/572,546

(22) Filed: May 15, 2000

(51) Int. Cl.[7] .............................................. A61B 17/00
(52) U.S. Cl. ..................... 606/1; 200/302.2; 200/512; 200/516; 606/167
(58) Field of Search .................. 606/1, 167; 200/302.2, 200/512, 516

(56) References Cited

U.S. PATENT DOCUMENTS

| | | | | |
|---|---|---|---|---|
| 3,959,610 A | * | 5/1976 | Finnegan et al. | ............ 200/512 |
| 4,349,712 A | * | 9/1982 | Michalski | .................... 200/512 |
| 4,771,139 A | * | 9/1988 | DeSmet | ...................... 200/516 |
| 4,794,215 A | * | 12/1988 | Sawada et al. | .......... 200/302.2 |
| 5,217,478 A | | 6/1993 | Rexroth | |
| 5,561,278 A | * | 10/1996 | Rutten | ......................... 200/512 |
| 5,613,599 A | * | 3/1997 | Inagaki et al. | .............. 200/512 |
| 5,712,543 A | | 1/1998 | Sjostrom | |
| 6,214,003 B1 | * | 4/2001 | Morgan et al. | ............... 606/41 |

OTHER PUBLICATIONS

Dyonics EP–1® Handpiece Membrane Switch, 5 Photographs, Mar., 2000.
Linvatec Handpiece Membrane Switch, 3 photographs Mar., 2000.

* cited by examiner

Primary Examiner—Lee Cohen
Assistant Examiner—Henry M. Johnson
(74) Attorney, Agent, or Firm—Flynn, Thiel, Boutell & Tanis, P.C.

(57) ABSTRACT

A surgical handpiece (20) for performing medical procedures. The handpiece (20) has a housing (24) and a membrane switch assembly (22) is mounted to the housing for regulating the operation of the handpiece. The membrane switch assembly has a switch plate (64) mounted in a cavity (42) formed in the housing. The switch plate includes a pair of spaced apart contact pads (86, 87). A dome (120) formed of flexible metal is spaced over the contact pads. A keypad (138) extends over the top of the switch cavity to cover the switch plate. A bezel plate (46) is fitted over the keypad. The keypad is compressed between the bezel plate and the housing to form a seal around the switch cavity. Depression of the keypad results in the dome flexing inwardly and closing the connection between the contact pads.

33 Claims, 10 Drawing Sheets

POWERED SURGICAL HANDPIECE WITH MEMBRANE SWITCH

FIELD OF THE INVENTION

This invention relates generally to powered surgical handpieces and, more particularly, to a powered surgical handpiece with a membrane switch that provides an audible and tactile indication of when the switch undergoes a state transition.

BACKGROUND OF THE INVENTION

In modern surgery, one of the most important instruments available to medical personnel is the powered surgical handpiece. Typically, this handpiece includes a housing that is held by a surgeon. Inside the handpiece is some type of power-generating unit. Often, this unit is a motor. However, the power-generating unit can also be a transducer that generates sonic energy or a light-emitting device that generates thermal energy. Usually some type of accessory is attached to the head end, also known as the distal end, of the handpiece. The accessory serves as the component that transfers the energy developed by the power-generating unit to the surgical site in order to accomplish the desired surgical procedure. For example burs, drill bits and shavers are attached to handpieces that contain motors. The motor rotates these accessories in order to cause the selected removal of tissue to which they are applied. Sonic and optical waveguides are attached to the distal ends of the handpiece that, respectively, have sonic and light generating units. These waveguides direct the energy that is transmitted through them to surgical sites so that the energy causes the desired end surgical affect.

The availability of powered surgical handpieces has made it possible to perform surgical procedures more quickly and more accurately than was previously possible with the manual handpieces that they replaced. Moreover, the availability of some powered surgical handpieces has made it possible to perform some surgical procedures that, previously, were difficult, if not impossible, to perform.

When constructing a powered surgical handpiece, it is often desirable to mount switches on the surface of the housing. Often, but not always, these switches are connected to a control console to which the handpiece is connected. The depression of the switches result in the change of the characteristics of the power signal that the control console applies to the handpiece's power generating unit. The modulation of this power signal causes the power generated by the handpiece to undergo a user-requested state change. These switches make it possible for the surgeon to, with a single hand, both control the position of the handpiece and the operation of its power-generating unit. Still another advantage of providing these switches is that they eliminate the need for the surgeon to have to verbally give commands to a technician who, in turn, manipulates switches or knobs on the control console in order to cause the desired state change of the handpiece power generating unit.

Currently, many handpieces are provided with carbon contact switch assemblies. This type of assembly includes a substrate. Each switch on the substrate includes two conductive surfaces that are separate from each other by a relatively small distance of 0.100 inches or less. A rubber or silicon rubber sheet is fitted over the substrate. This sheet forms the exposed outer body of the switch assembly. For each switch on the assembly, the rubber sheet is formed to have a raised boss that forms the portion of the switch that is manually depressed. This boss subtends the complementary conductive surface of the switch with which it is integral. A conductive member is mounted to the underside surface of the rubber sheet opposite the raised boss. This conductive member may be a carbon embedded pad or a disk of metal that is highly conductive. Normally, the conductive member is spaced away from the adjacent conductive surfaces on the substrate. However, the depression of the boss causes the rubber sheet to flex inwardly. This displacement of the rubber sheet results in the conductive pad coming into physical contact with the underlying, closely spaced conductive surfaces. As a result of this contact, the conductive pad completes the circuit between the substrate conductive surfaces. The completion of this circuit thus closes the connection controlled by the switch.

A disadvantage of the above described switch assembly is that the feedback it provides upon its transition from the open state to the closed state is nominal. Consequently, it is difficult for the surgeon to know whether or not the power generating unit has actually received a set of signals requiring it to undergo the state change the surgeon wanted to occur when he/she actuated the switch. Sometimes, because the surgeon did not know whether or not the switch was actuated, he/she may repeatedly depress the switch. This action can result in the handpiece power-generating unit undergoing state changes in excess of what the surgeon wanted.

It has been suggested that it would be useful to provide powered surgical handpieces with membrane type switches. A membrane switch has a small, flexible metal dome that is located over the complementary conductive surfaces on the underlying substrate. The flexing of the dome results in the dome establishing an electrical connection between the conductive surfaces on the substrate. Also, when the dome is flexed, a distinct "click" sound is heard and a distinct tactile is obtained by the person that depressed it. Collectively, this audible and tactile feedback provides the surgeon with an indication that the switch has closed the connection it is intended to establish.

However, to date, it has proven difficult to provide a handpiece with a membrane switch assembly. This is because, in order to be reused, a surgical handpiece is typically subjected to autoclaving in order to sterilize it. In autoclaving, the handpiece is placed in a chamber in which it is exposed to saturated steam which has a temperature of approximately 270° F. and is at a pressure of approximately 30 psi. This high temperature water vapor flows into most of the unsealed portions of the handpiece. If the metal parts forming a membrane switch are exposed to this water vapor, they will, in a relatively short time period, corrode. Moreover, when the other components of a membrane switch assembly are exposed to high temperatures, even in the absence of water vapor, they are likewise prone to break down. Consequently, while there have been some efforts to provide powered surgical handpieces with membrane switch assemblies, the end products have not proven particularly satisfactory.

SUMMARY OF THE INVENTION

This invention is related to a powered surgical handpiece with a membrane-type switch assembly. The individual switches of the assembly provide tactile feedback when the switches are depressed. The switch assembly of this invention is able to withstand the rigors of the sterilization process with the handpiece with which the assembly is integral.

BRIEF DESCRIPTION OF THE DRAWINGS

The invention is pointed out with particularity in the claims. The above and further features of the invention may be better understood by reference to the following description taken in conjunction with the accompanying drawings in which:

DETAILED DESCRIPTION

Figure 1:
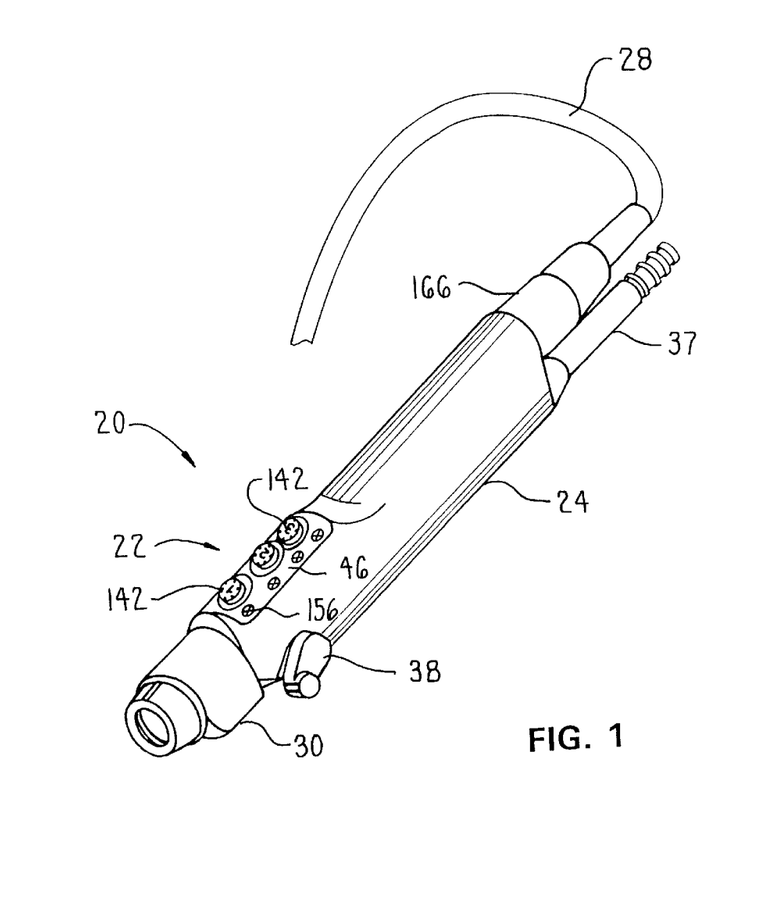
FIG. 1 is a perspective view of one type of powered surgical handpiece of this invention.
Figure 2:
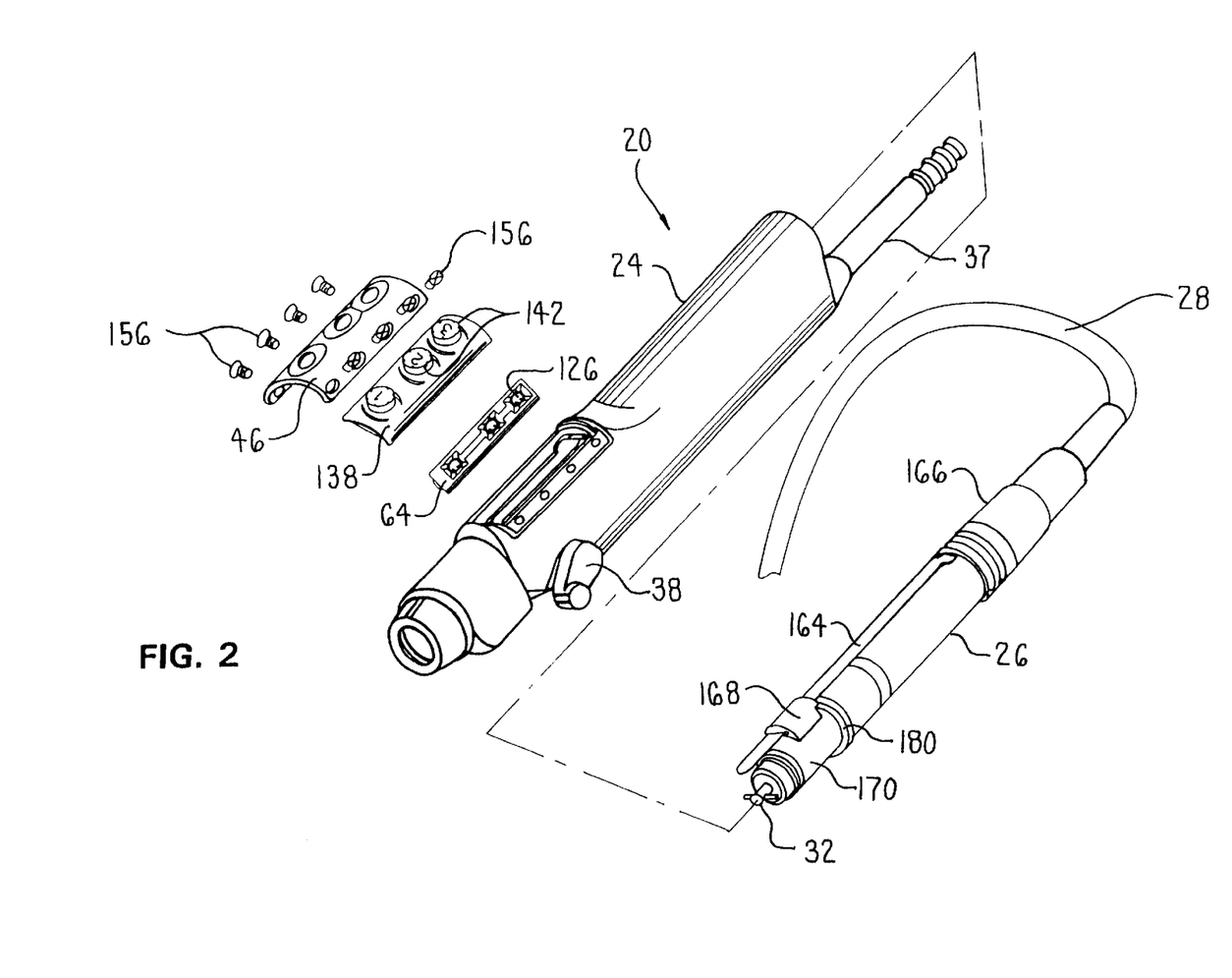
FIG. 2 is an exploded view of the handpiece of FIG. 1 in which the major sub-assemblies of the membrane switch assembly are depicted.

FIGS. 1 and 2 depict a powered surgical handpiece 20 of this invention that includes a membrane switch assembly 22. The particular handpiece 20 illustrated is referred to as a "shaver" and is used to perform endoscopic surgery. An understanding of endoscopic surgery can be obtained from the Applicant's Assignee's U.S. Pat. No. 5,850,496, entitled ENDOSCOPE WITH INTEGRATED, SELF-REGULATING LIGHT SOURCE, issued Dec. 15, 1998 which. is incorporated herein by reference. The handpiece 20 includes an elongated housing 24 that forms the body of the handpiece. An electric motor 26 is disposed in the housing 24. More particularly, the motor 26 is seated in a cylindrically shaped motor cavity 27 that extends forward from the rear, proximal end of the housing 24. Energization signals are applied to the motor 26 over a cable 28 attached to the proximal, rear end of the housing. The energizaton signals are generated by a control console (not illustrated) to which the opposed end of the cable 28 is connected. A coupling assembly 30 is mounted to the front, distal end of the housing 24. More specifically, coupling assembly 30 is mounted in a portion of the motor cavity 27 that extends rearwardly from the distal end of the housing 24. Coupling assembly 30 is used to releasably hold a cutting accessory (not illustrated) to the handpiece 20. When the cutting accessory is coupled to the handpiece 20, the accessory is fitted to an output drive shaft 32 that is connected to the rotor (not illustrated) integral with the motor 26. Actuation of the motor 26 results in rotational movement of the cutting accessory. The head end of the cutting accessory is applied to a surgical site in order to accomplish a desired surgical procedure.

Figure 3:
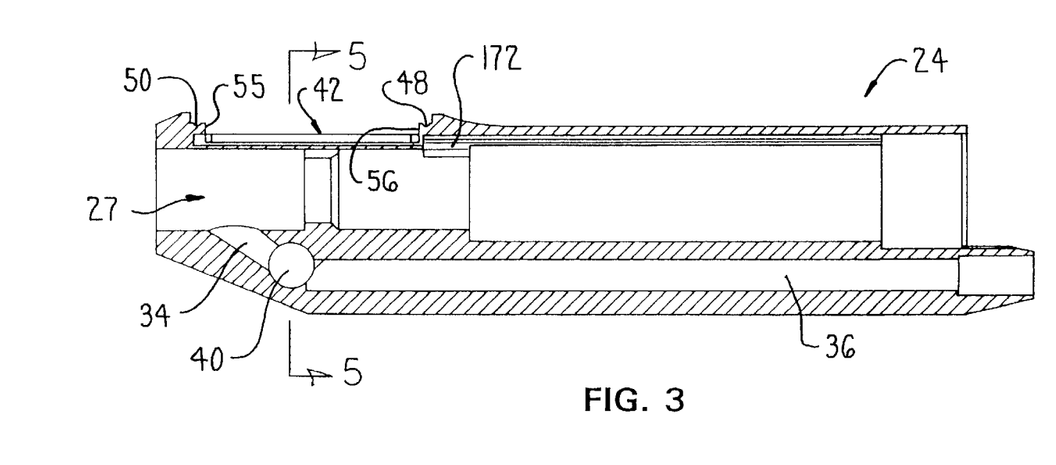
FIG. 3 is a cross sectional view of the housing of the handpiece of this invention.

The depicted housing 24, as seen in FIGS. 2 and 3, is also provided with a conduit through which suction may be drawn. It should be understood that the cutting accessories with which handpiece 20 are used typically have tubular bodies that are open at their proximal ends. The handpiece housing 24 is formed to have a pair of bores 34 and 36. Bore 34 extends diagonally rearwardly away from the motor cavity 27 at a location immediately rearward of the distal end of the housing. Bore 36, which runs parallel to the motor cavity 27, extends to the proximal end of the housing 24. A suction fitting 37 extends out of bore 36 beyond the proximal end of housing 24. When the handpiece 20 is in use a suction pump is connected to fitting 37 over a suction tube (pump and tube not illustrated). The suction drawn by the pump causes a suction flow from the front end of the cutting accessory, through the cutting accessory, the bores 34 and 36 and the suction tube to a receptacle integral with the pump. This suction flow is used to remove fluid and debris from the surgical site.

A valve 38 fitted to the housing 24 regulates the suction flow. Valve 38 is located in a valve chamber 40 formed in the housing 24 between bores 34 and 36. The position of the valve 38 in chamber 40 controls the magnitude of the suction flow.

Figure 4:
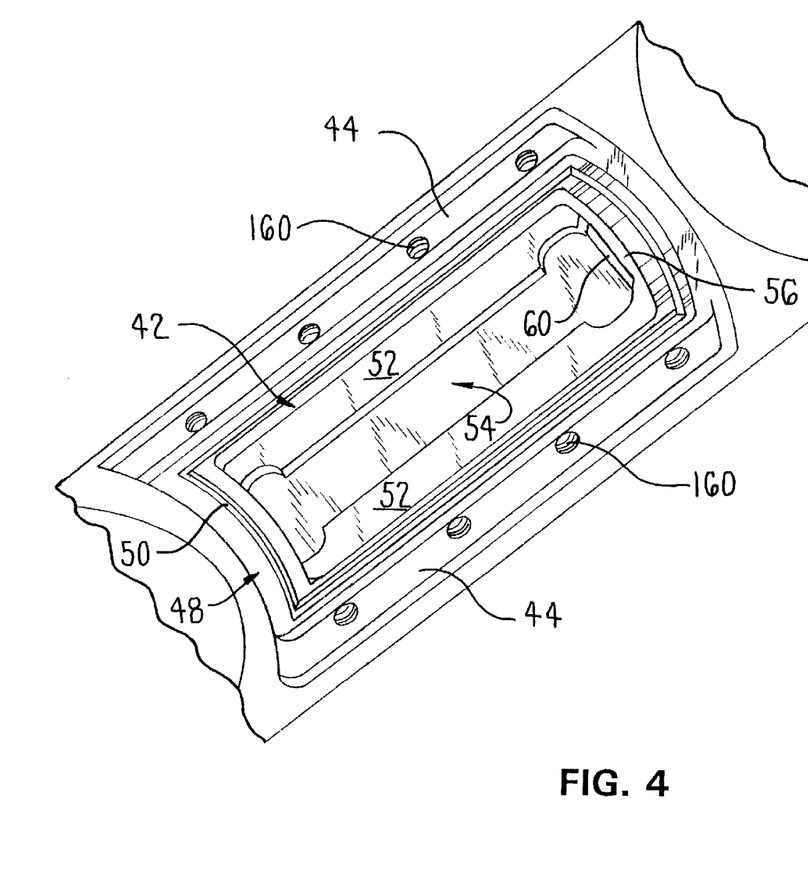
FIG. 4 is a top plan view looking into the switch cavity of the housing.
Figure 5:
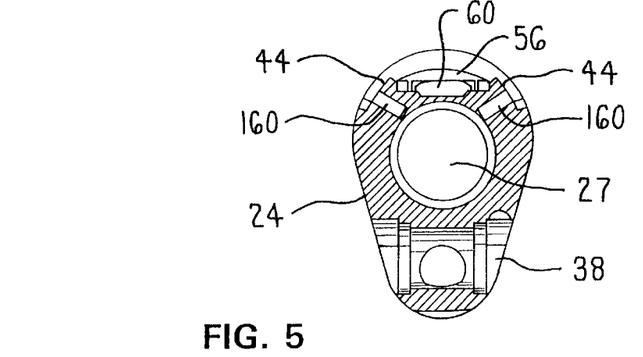
FIG. 5 is a section view of the handpiece looking rearwardly along line 5—5 of FIG. 3.

The membrane switch assembly 22 is seated in a switch cavity 42 formed in the housing 24. Specifically, the switch cavity 42, now described by reference to FIGS. 4 and 5, is an elongated space that is formed immediately rearwardly of the distal end of the housing 24. Specifically, housing 24 is formed so as to have two longitudinally extending, spaced apart outer steps 44. The outer steps are surfaces of the housing 24 that are recessed relative to the outer surface of the housing. As will be described hereinafter, the outer steps 44 are the surfaces of the housing 24 against which a bezel plate 46 (FIG. 2), which forms the outer body of the switch assembly 22, seats. Housing 24 is further formed so as to have an inner step 48 that extends between and is located adjacent to the outer steps 44. Inner step 48 is inwardly recessed relative to the outer steps 44. The inner step 48 is generally in the form of a rectangular frame. The inner perimeter of the inner step 48 defines the outer perimeter of switch cavity 42. The housing 24 is further formed so as to have a groove 50 that extends inwardly from the top surface of the inner step 48. Groove 50 extends circumferentially around the whole of the surface of inner step 48. It should further be understood that the housing 24 is formed so that the outer steps 44 and inner step 48 have an arcuate cross-sectional profile that approximates the curvature of the outer surface of the housing 24 from which the steps 44 and 48 are recessed.

Handpiece housing 24 is further formed so as to have two spaced-apart, longitudinally extending raised surfaces 52 that extend upwardly into the base of switch cavity 42. Collectively, the raised surfaces 52 define an elongated rectangular slot 54 that extends longitudinally and axially along the base of the switch cavity 42. The housing 24 is formed so as to have a front wall 55 that closes the front end of the switch cavity 42. Housing 24 has a rear wall 56 that defines the proximal end of cavity 42. Rear wall 56 is shaped to have an opening 60 that is aligned with and extend upwardly a small distance from the proximal end of slot 54. Opening 60 provides communication between motor cavity 27 and switch cavity 42.

Membrane switch assembly 22 includes a switch plate 64 now described by reference to FIGS. 6, 7A–7G and 8.

Figure 7A:
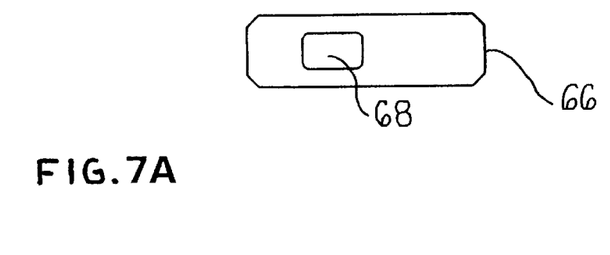
FIGS. 7A, 7B, 7C, 7D, 7E, 7F and 7G are plan views of the sheets of material that form the switch plate.

The switch plate 64 supports the conductive components of the switch assembly 22. A backing plate 66 (FIG. 7A)

serves as the support substrate for the remaining components of the switch plate 64. The backing plate 66 is formed of metal such as aluminum or other rigid material. In some versions of the invention, backing plate 66 is approximately 0.040 inches thick. The backing plate 66 is shaped to have a generally rectangular profile that facilitates the slip fitting of the plate in switch cavity 42. The corners of the backing plate 66 are, however, beveled to facilitate the insertion and removal of the switch plate 64 in the switch cavity. Generally, the layer components of the switch assembly 64 disposed on the backing plate 66 have a profile identical to that of the backing plate. The backing plate 66 is further formed to define an opening 68 that is slightly offset from the center of the plate. The reason for providing opening 68 is discussed below.

Figure 7B:
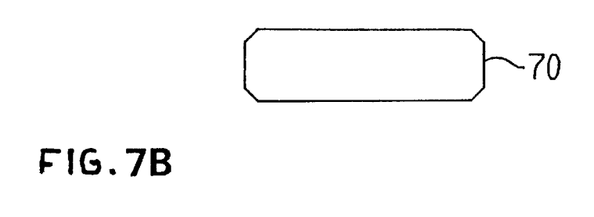
Figure 7C:
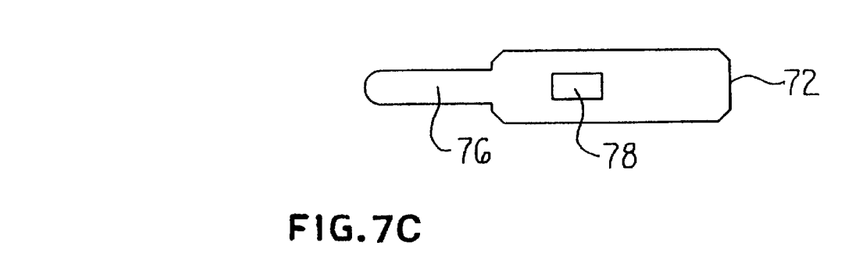

Immediately above the backing plate 66, switch plate 64 has a cover layer 70 (FIG. 7B). Cover layer 70 is formed of a dielectric material such as Kapton and in some versions of the invention is 0.002 inches thick. The cover layer 70 serves as a protective and insulating layer for the circuitry and components that are located above it. An insulating lamination layer 72 (FIG. 7C) is located above cover layer 70. Lamination layer 72 is formed from the same material of, and has the same thickness as, cover layer 70. The lamination layer covers, protects and insulates the next-described layer, the circuit layer 74. The lamination layer 72, like the layer it protects, is formed to have a stem section 76 that extends from one end of the main body of the layer. Lamination layer is further formed to define a rectangular center opening 78. Opening 78 of lamination layer 72 is positioned to be in registration with opening 68 of backing plate 66.

Figure 9:
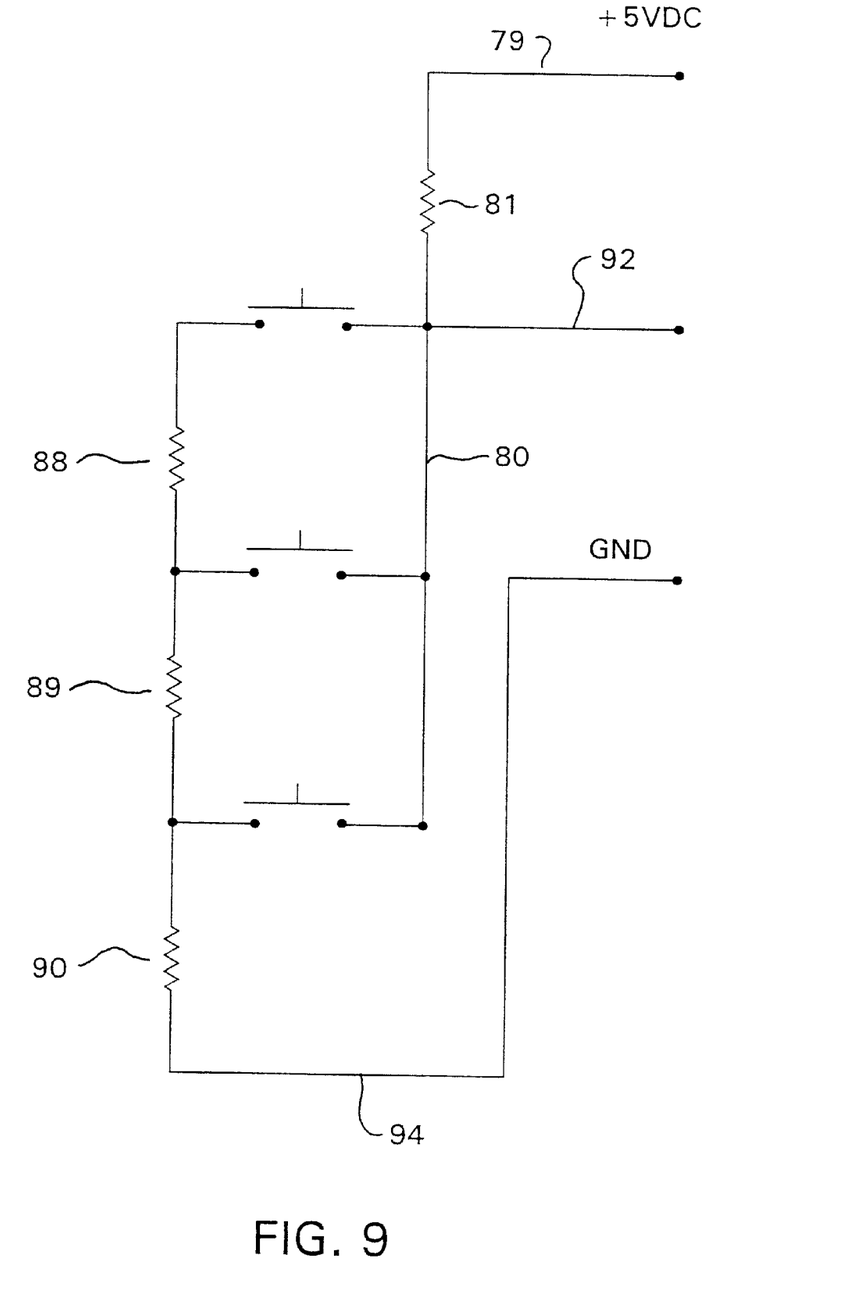
FIG. 9 is a schematic view of the circuit formed on the circuit layer of the switch plate.

The circuit layer, layer 74 (FIG. 7D) is the layer of switch plate 64.that physically carries the conductive components of the switch plate. Circuit layer 74 is a Kapton layer to which conductive traces have been selectively applied. The circuit formed on layer 74 is illustrated by FIG. 9. Specifically, there is a master bus 80 through which a reference signal flows. The reference signal is applied to bus 80 through a trace 79 and a resistor 81. In the illustrated version of this invention, this reference signal is a 5 VDC signal and resistor 81 is a 1 K Ohm resistor. The reference signal from bus 80 is applied to three generally rectangular conductive frames 86 formed on the outer, upper surface of circuit layer 74. The top of the conductive layer is further formed so that a conductive pad 87 is located in the center of each frame 86. It should be understood that each frame 86 and complementary pad 87 are physically spaced apart from each other. Also, there is a small opening in each frame 86 to provide a space for a trace connected to the associated pad 87.

Figure 7D:
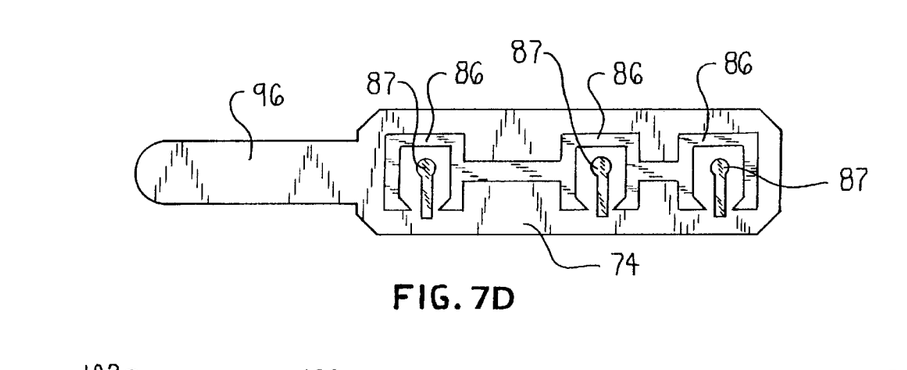

The conductive pads 87 are electrically connected to traces (not illustrated) located on the underside of circuit layer 74. More specifically, each pad 87 is connected to a separate resistor 88, 89 and 90 that is mounted to the underside of layer 74. Resistors 88, 89 and 90 are series connected together. The resistors 88, 89 and 90 have resistances of 365, 240 and 180 Ohms, respectively. Resistor 90 is connected to a trace 94 that leads to a ground plane. Trace 94 is located on the underside of the circuit layer 74. It should also be understood that resistors 81, 88, 89 and 90 are mounted to the underside of circuit layer 74.More particularly, the resistors are located on a surface of the underside of circuit layer 74 that is subtended by backing plate opening 68 and lamination layer opening 78.

Circuit layer 74, it will be further observed, is formed with a stem section 96. While not-seen in FIG. 7D, it should be understood that traces 79 and 94 extend outwardly on the stem section 96. There is also a third trace, trace 92. Trace 92 extends outwardly from the master bus 80.

An insulating and protective lamination layer 102 (FIG. 7E) is located over the circuit layer. Lamination layer 102 is formed from the same material as, and has the same thickness as, lamination layer 72. Lamination layer 102 is shaped to define three spaced apart rectangular openings 104. Each opening 104 is positioned to subtend a separate one of the conductive frames 86. Lamination layer 102 is also formed to define two channels 106 and 108. The channels 106 and 108 are narrower in width than openings 104. Channel 106 connects two adjacent openings 104. Channel 108 connects the other two openings 104. Lamination layer 102 has a. stem section 110 that extends over the top of cover layer stem section 96.

A cage layer 112 (FIG. 7F) is located above lamination layer 102. Cage layer 112 is formed from the same material as lamination layer 102. The material forming cage layer 112 has a thickness between 0.005 and 0.010 inches. The cage layer 112 has a rectangular shape that approximates that of the switch plate 64 or cover layer 70. Cage layer 112 is further shaped to define three openings 114 and two channels 116 and 118. Each opening 114 is positioned to be in registration over and has the same size as a separate one of the lamination layer openings 104. Channels 116 and 118 are positioned to be in registration over and subtend the same area as lamination layer channels 106 and 108, respectively.

Figure 6:
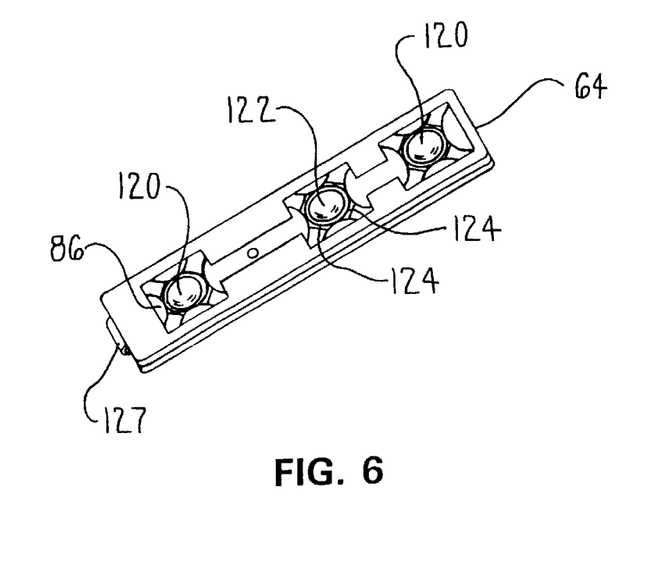
FIG. 6 is a perspective view of the switch plate of the membrane switch assembly.

Switch plate 64 is also provided with three domes 120. Each dome is formed of flexible metal such as stainless steel that is approximately 0.004 inches thick. The conductive metal forming the dome 120 has a click force of between 300 and 400 grams. Each dome 120 has a body 122 with a curved profile that approximates the curvature of a section of a sphere. Four legs 124, that are equangularly spaced, extend downwardly from the body 122. Each dome is seated over a separate one of the Ha conductive frames 86. The feet 124 of a dome physically abut the conductive material forming the associated frame. The dome body 122 normally extends over the conductive pad 87 centered in the frame 86. It should also be understood that each pair of lamination layer and cage layer openings 104 and 114, respectively, collectively define a space in which an associated one of the domes 120 is seated.

A cover layer 126 (FIG. 7G) extends over the cage layer 112 and is the topmost layer of the switch plate 64. Cover layer 126 is formed from the same material as and has the same thickness as the lamination layer 102. Cover layer 126 has the same basic shape as the first described cover layer 70. Cover layer 126 does, however, have a relatively short stem 127 that extends a short distance over lamination layer stem section 110. It will be observed that cover layer 126 extends over the tops of domes 120 so as to hold the domes in place. Cover layer 126 is formed with a small vent hole 128. Vent hole 128 is centered over cage layer channel 118. Vent hole 128 has a diameter of approximately 0.05 inches.

Figure 8:
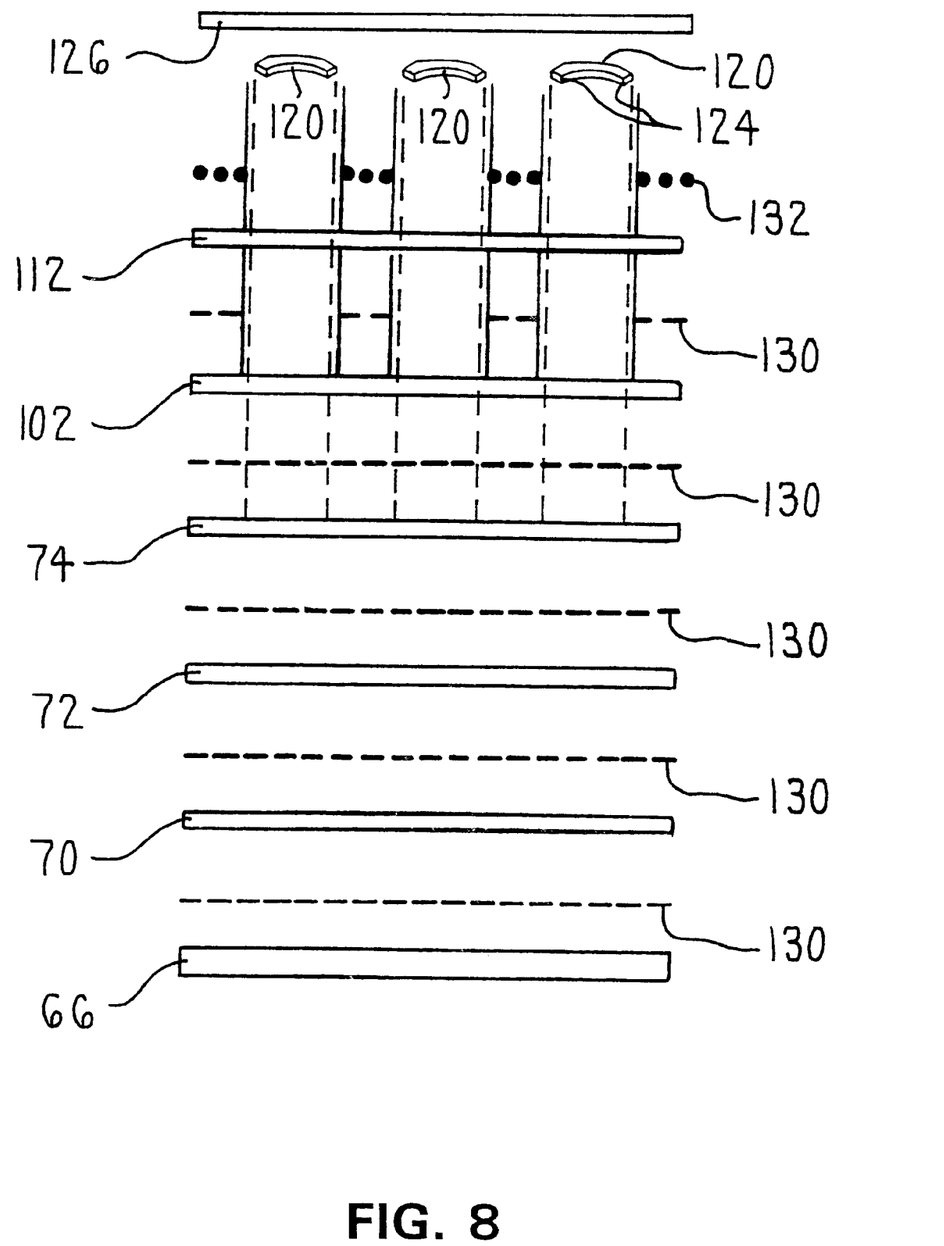
FIG. 8 is an exploded view depicting the relationship of the sheets of material that form the switch plate.

As represented by dashed lines 130 in FIG. 8, thermal sensitive adhesive is used to bond: cover layer 70 to backing plate 66; lamination layer 72 to cover layer 70; circuit layer 74 to lamination layer 72; lamination layer 102 to circuit layer 74; and cage layer 112 to lamination layer 102. However, a pressure sensitive adhesive, represented by dotted line 132 is used to bond cover layer 126 to cage layer 112. One suitable pressure sensitive adhesive that can be used to assemble handpiece 20 is available from the 3M Company of Minneapolis, Minn. as Transfer Tape Product No. 9461P.

Figures 7E, 7F:
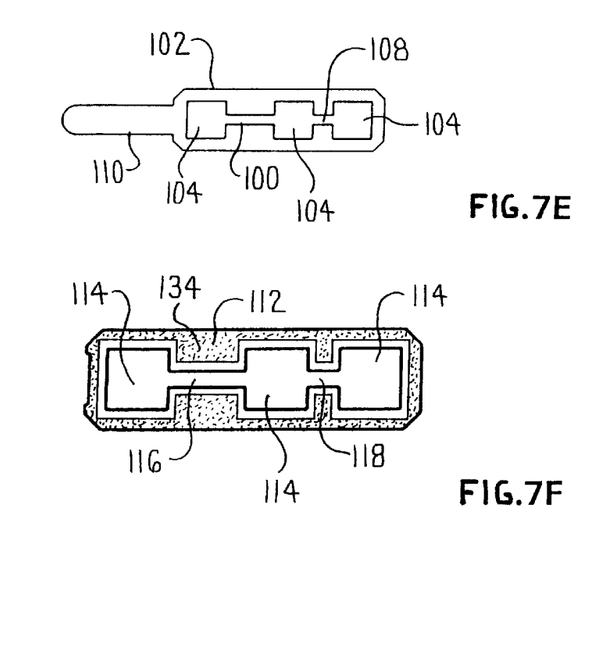
Figure 7G:
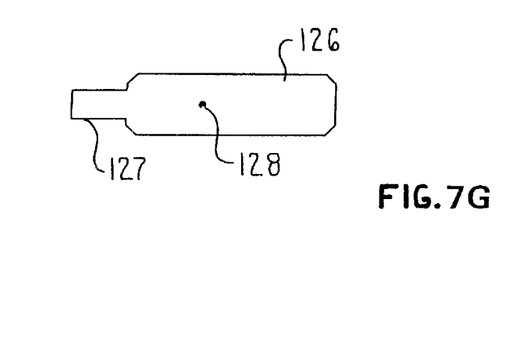

As seen by reference to FIG. 7F, in which the pressure sensitive adhesive is shown as a stippled surface 134, the adhesive is applied to the surface of cage layer 112 so that it is spaced away from the edges of the cage layer 112 that define openings 114. For example, in some versions of the invention, the pressure sensitive adhesive is applied to the cage layer 112 in such a manner that it is spaced between 0.020 and 0.025 inches away from the edges of the layer 112 that define openings 114.

Figure 10:
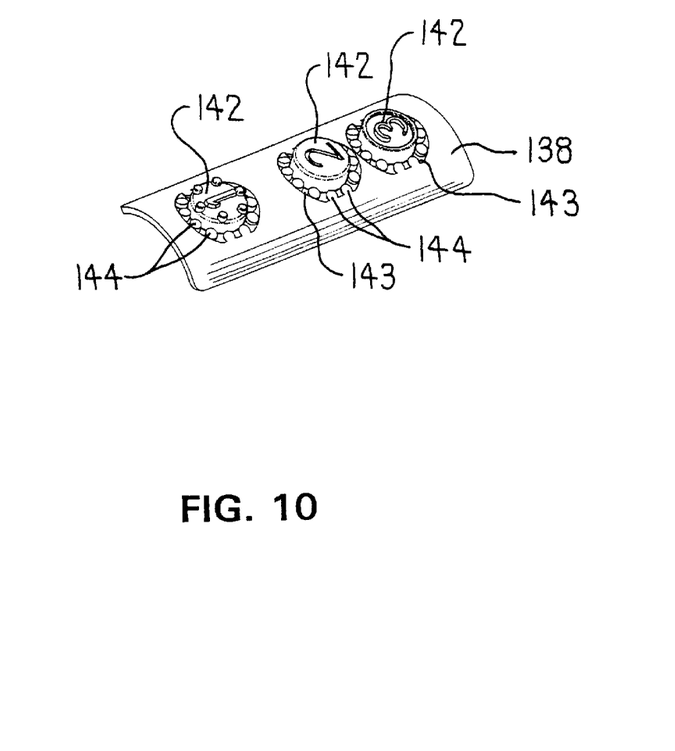
FIG. 10 is perspective view of the top of the keypad of the switch assembly.
Figure 11:
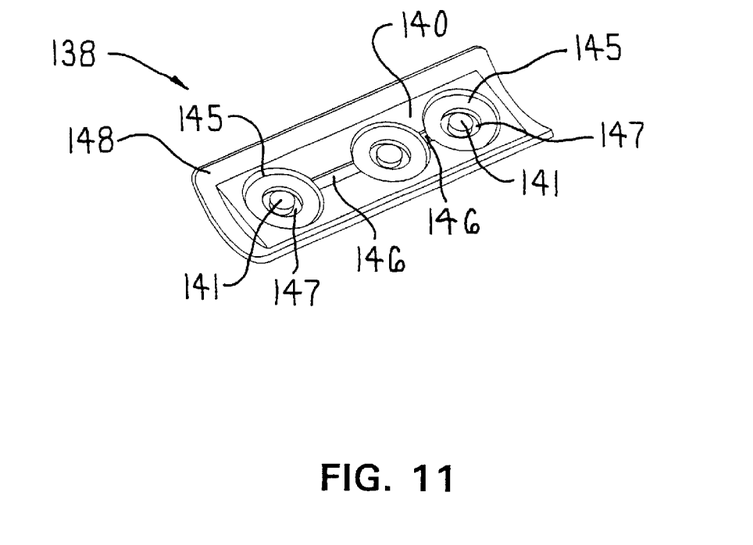
FIG. 11 a perspective view of the bottom of the keypad.

A keypad 138, now described by reference to FIGS. 10 and 11, covers the switch plate 64. The keypad 138 is formed from a single piece of flexible silicone rubber. The keypad 138 has a solid body 140. In cross section, keypad body 140 has a flat bottom surface and an opposed top surface that has an arcuate profile. Longitudinally, the keypad body 140 is shaped so that the body is able to snugly fit in switch cavity 42. Widthwise, the body 140 is shaped so as to not extend beyond the lateral perimeter of switch cavity 42. The keypad is further formed to have three solid, cylindrical heads that project upwardly from the top surface of the body 140. The heads are the individual buttons 142 of the switch assembly 22 that are selectively depressed. When the handpiece 20 is assembled, each button is in registration over a separate one of the domes 120. It will be further observed that the keypad body 140 is shaped so that the annular sections of material that surround buttons 142 are of reduced thickness so as to define annular recesses 143 around the buttons 142. Extending upwardly from the surfaces of the keypad body 140 that define recesses 143, the body is further formed to have a number of cylindrical bosses 144. The top surfaces of bosses 144 are generally flush with the top surfaces of the rest of the keypad body 140.

In the illustrated version of the invention, the top surfaces of the buttons 142 are formed to define identification numbers "1", "2" and "3". Also, the top surfaces of the buttons 142 are formed to have distinct profiles. The distal button 142 is formed with small, raised bosses 153 that surround its top surface and the identification number "1" is raised relative to the top surface. The middle button 142 has a smooth top surface and the identification number "2" is formed as a recess in the button. The proximal button 142 is formed with a raised lip around its outer perimeter and the identification number "3" is raised relative to its top surface. The individual buttons 142 are formed differently in order to provide a person using the handpiece 20 with different tactile impressions for each button. This feature of the invention is intended to minimize the extent to which a person has to look at a button in order to determine which button she is pressing.

The underside of the keypad is formed so that the body has three circular indentations 145. Each indentation subtends the area subtended by a corresponding one of the buttons 142. The circular indentations 145 are connected by channels 146. The keypad 138 is further formed so that centered within each indentation 145 is an even deeper counterbore 147. The counterbores 147 are concentric with the indentions with which the counterbores are associated. A small cylindrical plunger 141 extends outwardly from the base of each counterbore 147. The top of each plunger 141 is flush with the base surface of the associated indentation 145.

Keypad 138 is further shaped to have a lip 148 that extends outwardly beyond the perimeter of body 140. Lip 148 is shaped to have an arcuate shape. The arc inscribed by the keypad lip 148 is the arc inscribed by the space immediately above inner step 48 of the housing 24. Thus, lip 148 is dimensioned to seat upon the exposed top surface of inner step 48. Lip 148 is dimensioned to have a thickness that is slightly greater than the depth of the space in which it is seated. For example, in one version of the invention inner step 48 is recessed 0.033 inches relative to the adjacent outer steps 44. The keypad lip 148, which seats in this recessed space, has a thickness of 0.036 inches.

Figure 12A:
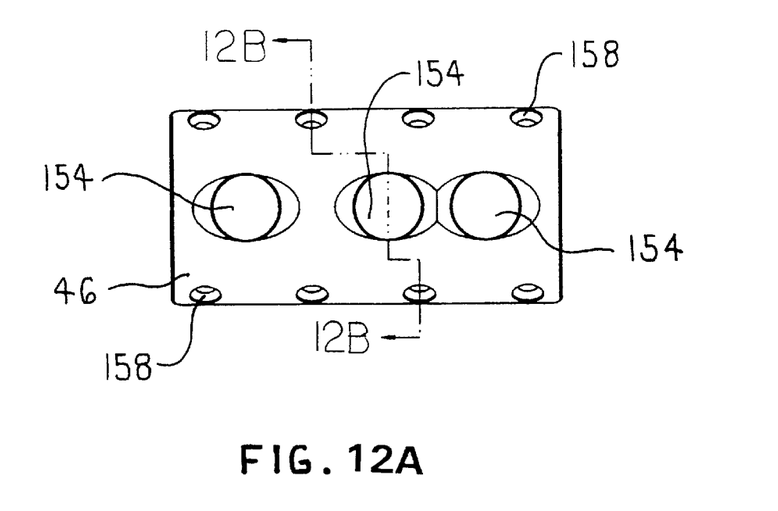
FIG. 12A is a top plan view of the bezel plate of the switch assembly.
Figure 12B:
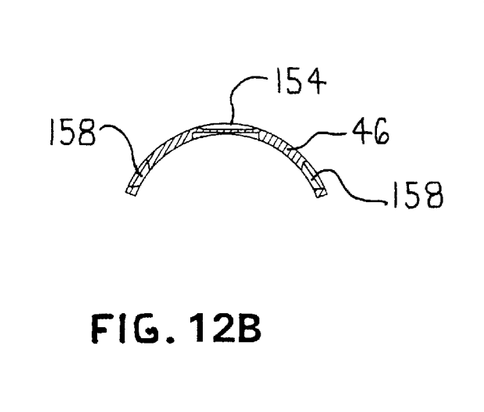
FIG. 12B is a cross-sectional view of the bezel plate taken along lines 12B—12B of FIG. 12A.

Bezel plate 46, illustrated in FIGS. 12A and 12B, seats over switch plate 64 and keypad 138. The bezel plate 46 is formed from hardened stainless steel. The bezel plate 46 is shaped to have a curved profile and is further dimensioned to seat immediately on top of the housing outer steps 44. Three openings 154 extend through the bezel plate 46. The openings are located along the longitudinal center axis of the bezel plate 46. Each opening 154 accommodates a separate one of the buttons 142 integral with keypad 138. Screws 156 (FIG. 2) secure the bezel plate 46 to the housing 24. The screws 156 extend through screw holes 158 formed in the side of the bezel plate 156 and fit into threaded bores 160 that extend inwardly from the housing inner steps 44.

Returning to FIG. 2, it can be seen that another component of the handpiece 20 of this invention is an elongated flex circuit 164. Flex circuit 164 extends forward from the distal end of the motor 26, through housing opening 60 into switch cavity 42. Flex circuit 164 carries conductors (not illustrated) that provide an electrical path between the switch plate 64 and a plug 166 mounted to the distal end of the motor 26. The plug 166 is the component to which cable 28 is connected. Thus, the flex circuit 164 serves as one of the conductive members through which signals are exchanged between the switch assembly 22 and the control console.

Figure 13:
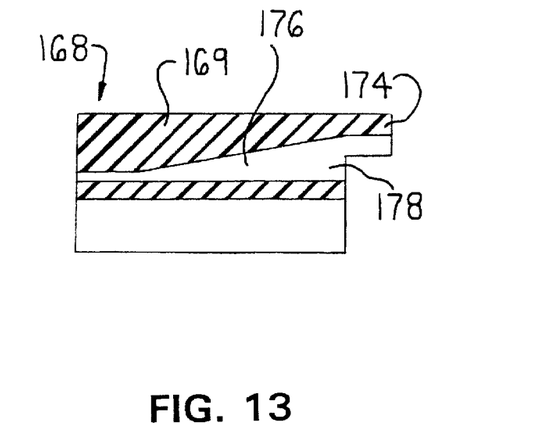
FIG. 13 is a cross-sectional view of a seal used to establish a hermetic barrier around the switch assembly.

The flex circuit 164 extends through a seal 168 now described by reference to FIGS. 2 and 13. Seal 168 is formed from silicone rubber. The seal 168 has a body 169 that is formed to have arcuately shaped top and bottom surfaces. More particularly, the seal body 169 is shaped so that the bottom surface has an arcuate profile that approximates the curvature of a forward section 170 of the housing in which the motor and associated reduction gears are seated. The top surface of the seal 168 is shaped to have a curvature that approximates that of a section 172 of the motor cavity 27 (FIG. 3) in which the seal is seated. Seal 168 is also shaped to have a tail section 174 that extends rearwardly from the proximal end of the seal body 169.

The seal 168 is shaped to have an elongated slot 176 that extends longitudinally through the body of the seal. More particularly, the seal 168 is formed so that its proximal end and the tail section 174 define a rear opening 178 into the slot that is relatively wide in the lateral direction. Forward from opening 178, slot 176 narrows in height. Adjacent the front of the seal, the seal is shaped so that slot 176 has dimensions that approximate that of the flex circuit 164.

Housing 24 is formed so that the motor cavity has a section 172 shaped to accommodate seal 168. Section 172 is located immediately rearwardly of housing rear wall 56.

When the handpiece 20 of this invention is assembled, seal 168 is fitted over flex circuit 164. The seal is positioned so that the tail section 174 seats against a shoulder 180 of the motor housing that defines the proximal end of the forward section 170 of the motor housing. Collectively, the housing 24, the seal 168 and the motor housing are shaped so that when the motor is completely positioned in the housing the longitudinal separation between the rear face of housing wall 64 and motor housing shoulder 180 is less than the length of the seal body 169. Consequently, when the motor 26, the flex circuit and the seal 168 sub assembly are fitted in housing 24, the seal body 169 is compressed between the housing rear wall 56 and the motor housing shoulder 180. This compression urges the front end of the seal body 169 rot against the adjacent surface of rear wall 56. The compression also urges the portions of the seal body 169 around the proximal portion of slot 176 against the flex circuit 164. As a consequence of the seal 168 abutting these surfaces, the seal forms a hermetic barrier around the flex circuit 164 and the opening 60 in the housing rear wall 56.

Handpiece 20 of this invention is assembled by positioning switch plate 64 in housing switch cavity 42. The switch plate 64 is oriented so that the stem sections 76, 96, 110 and 127 extend in the forward direction. More specifically, the stem sections 76, 96 and 110 are folded around the front end of plate 64 so as to be located underneath the backing plate 64. Conductive vias on circuit layer stem section 96 are bonded to complementary conductive pads on flex circuit 164 (vias and pads not illustrated). When the switch-plate 64 is fitted into switch cavity 42, the backing plate 66 seats on raised surfaces 52; the distal end of the flex circuit 164 and stem sections 76, 96 and 110 seat in slot 54.

After the switch plate 64 is connected to the flex circuit and seated in the switch cavity 42, keypad 138 is fitted in place over the switch plate., Keypad body 140 seats in the top of the switch cavity 42. The keypad lip 148 extends over and abuts housing inner step 48.

Bezel plate 46 is then fitted over switch plate 64 and keypad 138. More particularly, the handpiece housing 24 and bezel plate 46 are collectively dimensioned so that, eventually, as a result of screws 156 pushing the bezel plate downwardly, the inner surface of the bezel plate abuts the exposed surfaces of housing outer steps 44. Also, as a result of the pressure imposed on the key pad lip 148, a small rib like section of the lip is forced into groove 50.

Collectively, a single switch of assembly 22 consists of: a conductive frame 86 and its complementary conductive pad 87; the dome 120 that extends over the conductive frame; and the keypad button 142 and plunger 141 located over the dome. Resistor 82, in combination with resistors 88–90, form a variable resistance voltage divider. The closing of the switches determines which of the resistors 88, 89 and/or 90 are part of the voltage divider. The voltage between trace 92 and trace 94 serves as a measure of the resistance across the voltage divider. Therefore, the voltage across traces 92 and 94 serve as an indication of which of the switches is in the closed state.

When a surgeon wants to actuate one of the switches on switch assembly 22, he/she depresses the appropriate button 142. The button 142 will flex inwardly. The plunger 141 associated with the button 142 strikes the underlying dome 120 to cause the dome to flex inwardly. As a result of its inwardly flexing motion, the dome 120 strikes the underlying conductive pad 87. This contact closes the connection between the conductive pad 87 and the complementary frame 86. The closing of this connection results in the appearance of a defined voltage across trace 92 and ground trace 94. The control console, upon detecting this voltage, makes the appropriate adjustments to the power signal applied to the motor 26.

The flexing of the dome 120 also results in an audible, metallic "click" sound and a tactile change in resistance of the keypad button 142. This sound, since it is the result of the flexing of metal, is of relatively low frequency and this is an audibly distinct sound. Similarly, given the sudden change in resistance between when the dome is initially compressed and when it finally bends, flexes, the tactile feedback one receives upon its flexing is likewise clearly defined. Collectively, these sensory inputs provide the surgeon with an indication that the switch has closed in order to cause the desired change in the operating state of the handpiece 20.

Lamination layer channels 104 and 106, cage layer channels 116 and 118 and vent hole 128 collectively provide an air path from underneath the domes 120 to the space surrounding the switch plate 64. This air path serves two functions. Initially, when a downward force is imposed on a dome 120, it provides a path through which air underneath the dome is vented. This discharge path prevents the air from forming a high-pressure air mass that could inhibit the inward flexing of the dome. Secondly, when the surgeon releases pressure on the button 142 and the underlying dome 120, the air path serves as a conduit through which air flows into the interstitial space-between the circuit layer and the dome. The pressure head of this air flow provides a force that fosters the return of the dome 120 to its normal, convex profile. The return of the dome 120 to its normal state should, of course, be understood to open the circuit connection the dome established.

The compression of the keypad lip 148 between the housing 24 and bezel plate 46 and the compression of the portion of the keypad lip 148 in groove 50 causes the keypad to form a vapor-tight seal above the switch plate 64. Collectively, the keypad 138 and seal 168 provide hermetic barriers that prevent vapor from entering the switch cavity 42. These barriers prevent supersaturated water vapor from entering the switch cavity 42 where it can short circuit the components of the switch assembly 24.

Still another feature of the handpiece 20 of this invention is that the adhesive employed to secure most of the layers of material forming the switch plate 64 together is temperature sensitive adhesive. Once this adhesive is cycled through its high temperature-fostered curing process, the adhesive stays fixed in place. Subsequent heating of the handpiece 20, which occurs as a result of the handpiece being subjected to an autoclave sterilization, does not induce the reflowing of this adhesive. Consequently the adhesive does not flow into the space around the domes 120. If the adhesive were to flow into this space it could potentially adhere to the domes 120 or underlying surface of the circuit layer 74. If this event was to occur, upon the flexing of a dome 120, the adhesive could hold the dome in the flexed, switch closed, state. However, since the adhesive remains fixed during the sterilization process, the likelihood of this malfunction occurring is eliminated. However, as discussed above, pressure sensitive adhesive is employed to bond the cover layer 126 to cage layer 112. Pressure sensitive adhesive is employed to establish this bond because, after bonding, this adhesive will, to a limited degree, flex. The flexibility of this adhesive provides the cover layer with a limited degree of flexibility relative to the cage layer 112. This flexibility allows the cover layer to move to a limited extent whenever a keypad plunger 141 is depressed against it. By providing the cover layer with this range of movement, the extent to which-it becomes stressed when flexed is reduced. Since the stress to which the cover layer 126 is subjected to is reduced, the likelihood that, over time, the cover layer. may suffer structure failure is likewise minimized.

As discussed above, the pressure sensitive adhesive is applied to the cover layer 112 in the manufacturing process so that it is spaced away from the edges of the layer that define openings 114. This is because, during the sterilization process, the adhesive may flow. However, since the adhesive is initially located away from openings 114, the likelihood it will flow into the openings 114 is essentially eliminated.

This results in a like substantial elimination of the possibility of the adhesive coming into contact with the domes 120 and the potentially adverse affects caused by such contact.

Still another feature of the handpiece 20 of this invention is that when bezel plate 46 is screwed in place, the housing outer steps 44 limit the inward movement of the bezel plate. The limiting of this movement limits the extent to which the bezel plate 46 compresses the keypad 138 against the housing 24. The limiting of the extent to which the keypad 138 is compressed limits the extent to which it is subjected to mechanical stress. The minimization of this stress reduces the likelihood that, over time, the material forming the keypad 138 will crack or otherwise separate. Thus, this design ensures that the keypad maintains its structural integrity so that the keypad, in turn, maintains its vapor tight barrier around the switch cavity 42.

Also, when the handpiece 20 of this invention is assembled, the recesses 143 formed in the keypad body 140 and the bosses 144 integral with the recesses are located underneath the portions of the bezel plate 46 that defines the openings 154. At the completion of autoclaving, the air/vapor in the autoclave is removed by suction. This suction force has a tendency to urge the keypad buttons 142 outwardly. When this occurs, the bosses 144 are urged against the undersurface of the bezel plate 46. The abutment of the bosses 144 against the bezel plate limits the extent to which the thin walled section of keypad 138 that defines recesses 143 are pulled outwardly. Thus, the keypad 138 is constructed to have thin layers of material around the buttons 142. This feature makes it relatively easy to depress the buttons 142. The keypad 138 is further constructed to minimize the stress placed on these thin walled portions of the keypad as a result of the sterilization process. This feature reduces the likelihood that these sections of the keypad 138 will become stressed to the point at which they will separate. The prevention of this separation helps insure that the keypad 138 functions as a hermetic seal.

Collectively, the above described features of the housing 24, the bezel plate 46 and switch plate 64 ensure that-the components of the switch assembly of the handpiece 20 of this invention will continue properly even after the handpiece has been subjected to numerous autoclave sterilizations. Thus, the handpiece 20 of this invention, in addition to providing distinct feedback when one of its switches is actuated, can be subjected to the rigors of the sterilization process.

The foregoing description is limited to a preferred embodiment of this invention. It will be apparent, however, that. variations and modifications may be made to the invention with the attainment of some or all of the advantages of the invention. For example, while in the described version of the invention, switch assembly 22 has three switches, in other versions of the invention the assembly may have less than three or more than three switches. In the described version of the invention, a common reference signal is applied to each of the switches. In other versions of the invention, different signals may be applied to each of the switches. Also, in other versions of the invention, resistors may not be mounted to the switch plate 64. Alternatively, instead of being mounted to the underside surface of the circuit layer 74, the resistors may be mounted to the upper, outer surface. In still other versions of the invention, the switch assembly may not include any resistors or similar electrical components. Thus other circuits may be integrated into the switch assembly 22. These circuits simply include conductors that are connected to the conductive frame 86 and complementary contact pad 87.

In the described versions of the invention, each conductive frame 86 extends substantially around the outer perimeter of the complementary conductive pad 87. More particularly, the frame 86 extends at least 180° around the perimeter of the contact pad 87. This is exemplary, in other versions of the invention, the actual shapes of the two complementary contact pads that form the static elements of an individual switch may vary from what has been described and illustrated.

The materials from which the components of the switch assembly are formed may be different from what has been described. Also, in other versions of the invention, few or alternatively more layers of material may be employed to form the switch plate 64. The dimensions stated for the various components of this invention should likewise be understood to be merely exemplary.

Also, in not all versions of the invention may it be necessary to provide a vent hole in the top cover layer of the switch plate 64.

In some versions of the invention, a hermetic seal may both surround the flex circuit 164 and extend into the opening 60 between the motor cavity 27 and the switch cavity 42.

In other embodiments of the invention, the flex strip that carriers the conductors to the switch plate 64 through the opening 60 between the motor cavity 27 and the switch cavity 42 may extend from the switch plate 64. In the described version of the invention, the switch plate 64 is removably mounted in the handpiece 20. In other versions of the invention, the switch plate 64 or individual components thereof may be permanently mounted in the handpiece and are integrally formed with the handpiece housing 24.

Moreover, it should be recognized that the power consuming-energy producing unit integral with the handpiece 20 of this invention need not always be an electric motor. In other versions of the invention, this unit may be a pneumatically driven motor, a laser, an ultrasonic energy producing transducer or other device used to supply the energy needed to accomplish a specific surgical procedure. Thus, it is the object of the appended claims to cover all such variations and modifications as come within the true spirit and scope of this invention.

What is claimed is:

1. A surgical handpiece including:
   a housing, said housing including a switch cavity that is located inwardly from an outer surface of said housing;
   a power consuming-energy producing unit disposed in said housing; and
   a switch assembly mounted to said housing: said switch assembly including:
      a switch plate disposed in the switch cavity, said switch plate having: a circuit layer, said circuit layer having an outer surface, at least one pair of spaced apart conductive contact pads disposed on the outer surface; a dome formed of flexible, conductive metal that is seated on the outer surface of said circuit layer above said pair of contact pads, said dome having a normal state in which said dome is spaced from at least one of said contact pads and a flexed state in which said dome abuts both said contact pads to establish a conductive path between said contact pads; and a first cover layer formed of insulating material disposed over the outer surface of said circuit layer and said dome;
      a keypad formed from flexible, electrically insulating material disposed over the switch cavity of said housing, said keypad being formed with an upwardly extending button that is in registration over said dome; and a bezel plate disposed over said keypad, said bezel plate having an opening through which said button extends wherein, said bezel plate is secured to said housing so that said keypad is compressed between said housing and said bezel plate so that said keypad forms a seal over the switch cavity.

2. The surgical handpiece of claim 1, wherein: an interstitial space is located between the outer surface of said circuit layer and said dome; and said first cover layer is formed with a vent hole that is in air communication with the interstitial space.

3. The surgical handpiece of claim 2, wherein:

said circuit layer has an under surface opposite the outer surface;

at least one resistor is mounted to the under surface of said circuit layer, said resistor being connected to one of said contact pads;

a second cover layer is disposed over the under surface of said circuit layer and said resistor; and said second cover layer is attached to a backing plate formed of rigid material wherein said backing plate is formed with an opening and said second cover layer and said circuit layer are positioned over said backing plate so that said resistor and a section of said second cover layer extending over said resistor are disposed in the opening of said backing plate.

4. The surgical handpiece of claim 1, wherein a cage layer is disposed between the outer surface of said circuit layer and said first cover layer and said cage layer is formed to define an enclosed opening in which said dome is seated.

5. The surgical handpiece of claim 4, wherein: said cage layer is formed to define a channel that extends from the enclosed opening; and said first cover layer is formed with a vent hole that is communication with the channel of said cage layer.

6. The surgical handpiece of claim 4, wherein a pressure sensitive adhesive bonds said cover layer over said cage layer and said pressure sensitive adhesive is located on said cage layer so as to be spaced away from perimeter sections of said cage layer that define the enclosed opening.

7. The surgical handpiece of claim 6, wherein a thermal sensitive adhesive bonds said cage layer over said circuit layer.

8. The surgical handpiece of claim 1, wherein:

an inner wall of said housing partially defines the switch cavity;

conductive members extend through the inner wall of said housing, said conductive members being electrically connected to said contact pads on said circuit layer; and a hermetic seal extends around said conductive members and against the inner wall of said housing.

9. The surgical handpiece of claim 8, wherein:

said housing is shaped to have a main cavity separate from said switch cavity and said power consuming-energy producing unit is located in said main cavity; and the inner wall of said housing separates the switch cavity from the main cavity; and said conductive members extend from said switch cavity into the main cavity.

10. The surgical handpiece of claim 1, wherein:

said housing is formed to have a recess that surrounds the switch cavity, said recess having a depth that is less than the depth of said switch cavity;

said keypad is formed to have a body that is positioned to be seated in a top end of the switch cavity and a lip that extends around said body, said lip being dimensioned to be seated in the housing recess and being shaped to project above the housing recess; and said housing, said bezel plate and said keypad are collectively dimensioned so that, the abutment of said bezel plate against said housing limits the extent to which said keypad is compressed.

11. The surgical handpiece of claim 1, wherein said power consuming-energy producing unit is a motor.

12. The surgical handpiece of claim 1, wherein said keypad is formed to define a recess that circumferentially surrounds the button and to have a plurality of spaced apart members in said recess.

13. A surgical handpiece, said handpiece comprising:

a housing, said housing being shaped to define a main cavity and a switch cavity that is separate from the main cavity, wherein the switch cavity extends inwardly from an outer surface of said housing and the main cavity and the switch cavity are separated by an inner wall of said housing;

a power consuming-energy producing unit located in the main cavity of said housing; and a switch assembly, said switch assembly including:

a circuit layer seated in the switch cavity, said circuit layer having an outwardly directed outer surface, at least one pair of spaced-apart conductive contact pads formed on the outer surface;

an insulating layer formed of insulating material disposed over the outer surface of said circuit layer, said insulating layer being formed to define an opening that subtends said conductive pads of said circuit layer and a channel that extends from the opening;

a dome formed from rigid flexible, conductive material that is seated in the opening of said insulating layer so as to be in contact with the outer surface of said circuit layer, said dome having a normal state in which said dome is spaced from at least one said contact pad and a flexed state in which said dome electrically connects said contact pads together;

a cover layer disposed over said insulating layer and said dome so as to encase said dome in the opening of said insulating layer wherein said cover layer extends over the channel formed in said insulating layer and is formed to have a vent hole in communication with the channel;

a keypad formed of flexible, electrically insulating material that is fitted to an outer surface of said housing so as to extend over the switch cavity, said keypad being formed to have a button that is aligned over said dome; and a bezel plate formed of rigid material that is disposed over said keypad and that is secured to said housing, said bezel plate being formed with an opening through which said keypad button extends and wherein said keypad is compressed between said housing and said bezel plate so that said keypad forms a seal between said housing and said bezel plate.

14. The surgical handpiece of claim 13, wherein said insulating layer is formed from a plurality of layers of electrically insulating material.

15. The surgical handpiece of claim 13, wherein a pressure sensitive adhesive bonds said cover layer over said insulating layer and said pressure sensitive adhesive is located on said insulating layer so as to be spaced away from perimeter sections of said insulating layer that define the opening.

16. The surgical handpiece of claim 15, wherein a thermal sensitive adhesive bonds said insulating layer over said circuit layer.

17. The surgical handpiece of claim 13, wherein:

said circuit layer is formed from flexible material; and said circuit layer is bonded to a rigid backing plate that is seated in the switch cavity.

18. The surgical handpiece of claim 13, wherein:

said housing, said bezel plate and said key pad are collectively shaped so that at least portions of said bezel plate extend beyond said keypad and abut said housing; and said housing, said bezel plate and said keypad are collectively dimensioned so that, the abutment of said bezel plate against said housing limits the extent to which said keypad is compressed.

19. The surgical handpiece of claim 18, wherein:

said housing is shaped to have a recess that surrounds the switch cavity; and said keypad is formed to have an outer lip and is shaped so that said lip seats in the recess of said housing.

20. The surgical handpiece of claim 13, wherein a first one of said contact pads at least substantially surrounds the other one of said contact pads.

21. The surgical handpiece of claim 13, wherein:

said circuit layer is provided with plural pairs of contact pads;

said insulating layer is formed with plural openings, each opening subtending one pair of said contact pads and the channel extends between the openings;

a separate said dome is seated in each opening of said insulating layer; and said keypad is formed to have a plurality of separate buttons each said button being aligned over as a separate one of said domes so that each said pair of contact pads, said dome associated with said contact pads and said button disposed over the said dome form a separate switch.

22. The surgical handpiece of claim 21, wherein two said contact pads that are each part of a separate said pair of contact pads are electrically connected together.

23. The surgical handpiece of claim 13, wherein said power consuming-energy producing unit is a motor.

24. The surgical handpiece of claim 13, wherein:

said inner wall of said housing is formed with an opening;

a conductor extends through the opening in said inner wall of said housing and is connected to one of said contact pads on said circuit layer; and a seal extends around said conductor and is located against said inner wall of said housing.

25. A surgical handpiece, said surgical handpiece comprising:

a housing, said housing having a switch cavity that extends inwardly from an outer surface of said housing and a recess that is located around the switch cavity, wherein the switch cavity and the recess each have a depth and the depth of the recess is less than the depth of the switch cavity;

a power consuming-energy producing unit disposed in said housing in a space separate from the switch cavity;

a bezel plate secured to an outer surface of said housing so as to extend over the switch cavity wherein said bezel plate abuts an outer surface of said housing adjacent the recess and said bezel plate is formed with an opening;

a keypad formed of electrically insulating, flexible material that is located between said housing and said bezel plate, wherein said keypad is shaped to have: a lip that extends around an outer perimeter of said key pad, said lip being shaped to seat in the recess of said housing; and a button, said button being positioned to extend through the opening in the bezel plate, and said housing, said bezel plate and said keypad are collectively dimensioned so that when said bezel plate abuts said housing, said lip is compressed between said housing and said bezel plate so that said keypad lip forms a seal around the switch cavity;

a switch plate disposed in the switch cavity of said housing, said switch plate having: substrate with an outer surface; a pair of spaced apart contact pads formed on the outer surface of said substrate, said contact pads being aligned with said keypad button; a dome formed from flexible, conductive material that is disposed over said contact pads, said dome having a normal state in which said dome is spaced apart from at least one said contact pad and a flexed state in which said dome physically abuts and is electrically connected to both said contact pads, wherein said dome is in registration with said keypad button so that, upon depression of said button, said button forces said dome from the normal state to the flexed state; and a cover disposed over said substrate and said dome, said cover having a vent port in air communication with an interstitial space between the substrate outer surface and said dome.

26. The surgical handpiece of claim 25, wherein:

an insulating layer is located between said substrate and said cover, said insulating layer being formed to define an opening in which said dome is seated and to define a channel that extends from the opening; and said cover is formed so that the vent hole is in registration with the channel defined by said insulating layer.

27. The surgical handpiece of claim 25, wherein said housing, said bezel plate and said keypad are collectively dimensioned so that, the abutment of said bezel plate against said housing limits the extent to which said keypad is compressed.

28. The surgical handpiece of claim 25, wherein:

said housing has an interior wall that partially defines said switch cavity, said interior wall being formed with an opening;

a conductive member extends through the opening in said housing interior wall and said conductive member is attached to at least one of said contact pads; and a seal extends around the opening in said housing interior wall and around said conductive member.

29. The surgical handpiece of claim 25, wherein said substrate is formed from a layer of flexible material and said substrate is secured to a backing plate that is seated in the switch cavity.

30. The surgical handpiece of claim 25, wherein at least one resistor is mounted to said substrate, said resistor being connected to at least one of said contact pads.

31. The surgical handpiece of claim 30, wherein said resistor is mounted to an underside of said substrate that is opposite the outer surface.

32. The surgical handpiece of claim 30, wherein:

said substrate is formed from a layer of flexible material and has an underside that is opposite said outer surface;

said resistor is mounted to the underside of said substrate;

said substrate is mounted to a rigid backing plate so that the underside of said substrate faces said backing plate and said backing plate is formed with an opening and said substrate is mounted to said backing plate so that said resistor is seated in the opening of said backing plate.

33. The surgical handpiece of claim 25, wherein said power consuming-energy producing unit is a motor.

\* \* \* \* \*